(12) United States Patent
Jeon et al.

(10) Patent No.: US 11,667,891 B2
(45) Date of Patent: Jun. 6, 2023

(54) METHOD OF SELECTIVELY DIFFERENTIATING UNDIFFERENTIATED MACROPHAGE INTO M1 MACROPHAGE

(71) Applicant: KOREA INSTITUTE OF SCIENCE AND TECHNOLOGY, Seoul (KR)

(72) Inventors: Hojeong Jeon, Seoul (KR); Youngmin Seo, Seoul (KR); Hyunseon Seo, Seoul (KR); Myoung-Ryul Ok, Seoul (KR); Yu Chan Kim, Seoul (KR); Hyun Kwang Seok, Seoul (KR); Seung Ja Oh, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 354 days.

(21) Appl. No.: 16/898,072

(22) Filed: Jun. 10, 2020

(65) Prior Publication Data
US 2020/0407684 A1 Dec. 31, 2020

(30) Foreign Application Priority Data
Jun. 27, 2019 (KR) .......... 10-2019-0077180

(51) Int. Cl.
| | |
|---|---|
| *C12N 5/0786* | (2010.01) |
| *C12M 1/42* | (2006.01) |
| *C12M 1/34* | (2006.01) |
| *C12M 1/12* | (2006.01) |
| *C12N 5/078* | (2010.01) |

(52) U.S. Cl.
CPC .......... *C12N 5/0645* (2013.01); *C12M 25/02* (2013.01); *C12M 35/04* (2013.01); *C12M 41/40* (2013.01); *C12N 5/0643* (2013.01); *C12N 2506/115* (2013.01); *C12N 2521/00* (2013.01); *C12N 2533/30* (2013.01)

(58) Field of Classification Search
CPC .......... C12N 5/0645; C12N 2506/115; C12N 2521/00; C12N 2533/30; C12M 25/02; C12M 35/04; C12M 41/40
See application file for complete search history.

(56) References Cited

FOREIGN PATENT DOCUMENTS

| KR | 10-1754798 B1 | 7/2017 |
|---|---|---|
| KR | 10-2019-0135733 A | 12/2019 |

OTHER PUBLICATIONS

Hayakawa et al. Optimal compressive force accelerates osteoclastogenesis in RAW264.7 cells. Molecular Medicine Reports 12: 5879-5885 (Year: 2015).*
Adams et al. Mechano-Immunomodulation: Mechanoresponsive Changes in Macrophage Activity and Polarization. Annals of Biomedical Engineering, vol. 47, No. 11. (Year: 2019).*
Sun et al. A simple and effective pressure culture system modified from a transwell cell culture system. Biol Res 46: 47-52. (Year: 2013).*
Hasel et al. A cell-culture system for long-term maintenance of elevated hydrostatic pressure with the option of additional tension. Journal of Biomechanics 35 (2002) 579-584 (Year: 2002).*
Bi et al. Alginate enhances Toll-like receptor 4-mediated phagocytosis by murine RAW264.7 macrophages. International Journal of Biological Macromolecules 105 (2017) 1446-1454 (Year: 2017).*
Cho et al. Compressive Mechanical Force Augments Osteoclastogenesis by Bone Marrow Macrophages Through Activation of c-Fms-Mediated Signaling. Journal of Cellular Biochemistry 111:1260-1269 (Year: 2010).*
Harwani, S. C., "Macrophages Under Pressure: The Role of Macrophage Polarization in Hypertension," Transl. Res. (2018), vol. 191, pp. 45-63.
Lassus et al., "Macrophage Activation Results in Bone Resorption," Clinical Orthopaedics and Related Research (1998), vol. 352, pp. 7-15.
McEvoy et al., "Synergistic Effect of Particles and Cyclic Pressure on Cytokine Production in Human Monocyte/Macrophages: Proposed Role in Periprosthetic Osteolysis," Bone (2002), vol. 30, No. 1, pp. 171-177.
Notice of Allowance dated Mar. 24. 2021, in Republic of Korean Patent Application No. 10-2019-0077180.
Office Action dated Nov. 30, 2020, in Republic of Korean Patent Application No. 10-2019-0077180.

* cited by examiner

*Primary Examiner* — Taeyoon Kim
(74) *Attorney, Agent, or Firm* — Birch, Stewart, Kolasch & Birch, LLP

(57) ABSTRACT

Provided is a method for the selective differentiation into M1 macrophages under a pressurized environment, and more particularly, a method for the selective differentiation of undifferentiated macrophages into M1 macrophages, the method including incubating the undifferentiated macrophages in an incubator under the pressurized environment. In addition, provided is a method for producing osteoclasts, the method including: incubating undifferentiated macrophages in an incubator under a pressurized environment to differentiate into M1 macrophages; and differentiating the differentiated M1 macrophages into osteoclasts.

2 Claims, 15 Drawing Sheets

Specification includes a Sequence Listing.

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Forward primer for HIF-1

<400> SEQUENCE: 1
cttgacaagc tagccggagg                                          20

<210> SEQ ID NO 2
<211> LENGTH: 21
<212> TYPE: DNA
<213> ORGANISM: Artificial Sequence
<220> FEATURE:
<223> OTHER INFORMATION: Reverse primer for HIF-1

<400> SEQUENCE: 2
tcgacgttca gaactcatcc t                                        21

<210> SEQ ID NO 3
<211> LENGTH: 21
<212> TYPE: DNA
<213> ORGANISM: Artificial Sequence
<220> FEATURE:
<223> OTHER INFORMATION: Forward primer for NOS2

<400> SEQUENCE: 3
tgccagggtc acaactttac a                                        21

<210> SEQ ID NO 4
<211> LENGTH: 20
<212> TYPE: DNA
<213> ORGANISM: Artificial Sequence
<220> FEATURE:
<223> OTHER INFORMATION: Reverse primer for NOS2

<400> SEQUENCE: 4
ctctccactg ccccagtttt                                          20

<210> SEQ ID NO 5
<211> LENGTH: 20
<212> TYPE: DNA
<213> ORGANISM: Artificial Sequence
<220> FEATURE:
<223> OTHER INFORMATION: Forward primer for Arg1

<400> SEQUENCE: 5
acggcagtgg ctttaacctt                                          20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for Arg1

<400> SEQUENCE: 6
aggtagtcag tccctggctt                                          20

<210> SEQ ID NO 7
<211> LENGTH: 20
<212> TYPE: DNA
<213> ORGANISM: Artificial Sequence

```
<220> FEATURE:
<223> OTHER INFORMATION: Forward primer for NFATc1

<400> SEQUENCE: 7
ttcgagttcg atcagagcgg                                              20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for NFATc1

<400> SEQUENCE: 8
cgagccaggt atcttcggtc                                              20

<210> SEQ ID NO 9
<211> LENGTH: 21
<212> TYPE: DNA
<213> ORGANISM: Artificial Sequence
<220> FEATURE:
<223> OTHER INFORMATION: Forward primer for TRAP

<400> SEQUENCE: 9
agcagctccc tagaagatgg a                                            21

<210> SEQ ID NO 10
<211> LENGTH: 20
<212> TYPE: DNA
<213> ORGANISM: Artificial Sequence
<220> FEATURE:
<223> OTHER INFORMATION: Reverse primer for TRAP

<400> SEQUENCE: 10
gtaggcagtg accccgtatg                                              20

<210> SEQ ID NO 11
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 11
ggcaaattca acggcacagt                                              20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 12
tagggcctct cttgctcagt                                              20
```

METHOD OF SELECTIVELY DIFFERENTIATING UNDIFFERENTIATED MACROPHAGE INTO M1 MACROPHAGE

CROSS-REFERENCE TO RELATED APPLICATION

This application claims priority to Korean Patent Application No. 10-2019-0077180 filed on Jun. 27, 2019 and all the benefits accruing therefrom under 35 U.S.C. § 119, the contents of which are incorporated by reference in their entirety.

BACKGROUND

The present disclosure relates to a method for the selective differentiation into M1 macrophages, and more particularly, to a method for the selective differentiation into M1 macrophages by applying pressure to cells.

Cancer is the most common cause of death in Korean, and has been reported as the top three leading causes of death together with cerebrovascular disease and heart disease. Accordingly, the anticancer agent market accounts for the highest share in the global pharmaceutical market according to global pharmaceutical market research results for each efficacy group. In addition, methods such as surgery, chemotherapy, and radiotherapy for treating cancer have been used. However, the traditional anticancer therapy has a serious limitation of therapy due to accompanying side effects such as immunity decrease in a long-term period. An effective anticancer agent has been urgently required to be developed, and an immunological therapy having relatively low side effects and excellent efficacy has been emerged as an alternative.

Meanwhile, macrophages are representative immune cells which are derived from bone marrow cells and responsible for the main function of innate immunity, and the macrophages initially come out of the bone marrow in the form of monocytes in an immature state through the bloodstream. The monocytes are differentiated into mature macrophages by increased activity in the process of recognizing byproducts or pathogens derived from infected cells. Macrophages have an important function for maintaining homeostasis of tissues by eliminating pathogens invading from the outside and inducing adaptive immunity, and play an important role in the early stage of an inflammatory response in the human body, and the macrophages are matured in two types, specifically, M1 macrophages (classically activated macrophages) and M2 macrophages (alternatively activated macrophages) according to their differentiation method. Among them, M1 macrophages are macrophages that recognize and remove external organisms, bacteria, viruses, etc., and efficiently kill and defend cancer cells. Therefore, development of a cell differentiation method capable of effectively differentiating macrophages into M1 macrophages is urgent in order to develop a cancer immunotherapeutic agent. In this regard, Korean Patent No. 10-1754798 discloses a composition for inducing the differentiation into M2 macrophages including mesoporous silica nanoparticles in which cytokine is contained.

SUMMARY

However, the related art is a technique for the differentiation into M2 macrophages, and a differentiation technique into M1 macrophages which are innate immune cells important for anticancer and anti-inflammation responses does not exist yet.

The present disclosure has been made to solve various problems including the above problems, and an object of the present disclosure is to provide a method for the selective differentiation into M1 macrophages, the method being capable of effectively differentiating into innate immune cells by applying pressure to macrophages. However, the object is for illustrative purpose only and the scope of the present disclosure is not limited thereby.

The present disclosure provides a method for the selective differentiation of undifferentiated macrophages into M1 macrophages, the method including incubating the undifferentiated macrophages in an incubator under a pressurized environment.

The present disclosure also provides a method for producing osteoclasts, the method including: incubating undifferentiated macrophages in an incubator under a pressurized environment to differentiate into M1 macrophages; and differentiating the differentiated M1 macrophages into osteoclasts.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
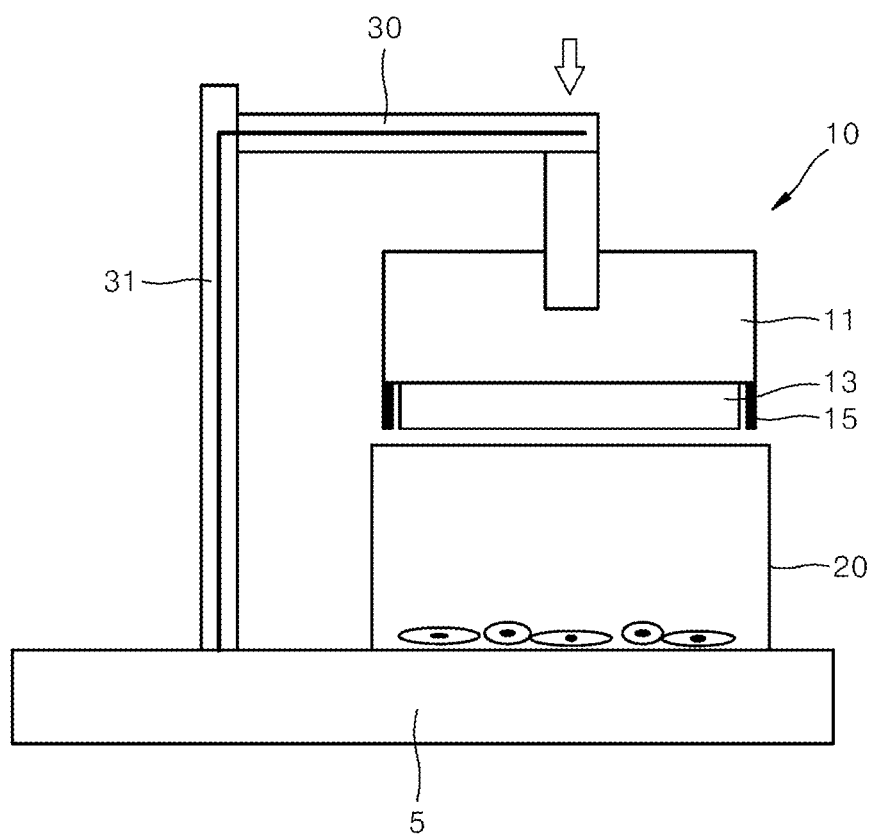
FIG. 1 is a schematic view illustrating a configuration of a cell incubator under a pressurized environment to provide pressure for macrophages in accordance with an exemplary embodiment of the present disclosure.

Hereinafter, specific embodiments will be described in detail with reference to the accompanying drawings.

Definition of Terms

As used herein, the term "M1 macrophage" refers to a classically activated macrophage, and is a macrophage having a known functional characteristic of macrophages, i.e., a function that recognizes and removes external organisms, bacteria, viruses, etc. and efficiently kill and prevent cancer cells.

As used herein, the term "osteoclast" refers to a giant cell which has a diameter of 20-100 µm, contains about 50 nuclei and is closely related to bone resorption. The osteoclast causes osteoporosis, and is not cultured by the present technology. Therefore, the osteoclast is not being sold as a cell line, and thus the research on related fields is being significantly affected.

DETAILED DESCRIPTION OF THE INVENTION

The present disclosure provides a method for the selective differentiation of undifferentiated macrophages into M1 macrophages, the method including incubating the undifferentiated macrophages in an incubator under a pressurized environment.

In the method for the differentiation, the pressurized environment may be created by a transwell which vertically descends from an upper portion of the incubator to the inside of the incubator to mechanically press the top surface of cells, or by injecting pressurized air into a chamber of the incubator, wherein the transwell may include a hollow chamber, a membrane which is provided in an upper side of an empty space of the chamber and is composed of a porous film, and a hydrogel attached to a lower portion of the membrane.

Optionally, it is possible to pressurize the top surface of cells by a pressing plate of which the height is regulated and in which the hydrogel is attached to the bottom surface thereof, instead of the transwell.

In the method for the differentiation, the pressurized air may have an atmospheric pressure of 1.5-5, the hydrogel may be formed by hydration of a natural or synthetic polymer exhibiting a negative charge, and the natural or synthetic polymer exhibiting the negative charge may be carrageenan, alginate, xanthan gum, gellan gum, polyacrylic acid, heparin, or carboxymethylcellulose.

In the method for the differentiation, the undifferentiated macrophages may be monocyte-derived undifferentiated macrophages or bone marrow-derived undifferentiated macrophages.

The present disclosure also provides a method for producing osteoclasts, the method including: incubating undifferentiated macrophages in an incubator under a pressurized environment to differentiate into M1 macrophages; and differentiating the differentiated M1 macrophages into osteoclasts.

In general, an articular cartilage is adapted to an environment exposed to pressurization in a human body and plays a role in absorbing an impact and preventing abrasion of a joint during joint movement, and thus, the articular cartilage may be defined as a pressurized-environment cell. When these cells are cultured on a two-dimensional surface to increase the growth rate, there is a concern that cartilage cells lose their intrinsic characteristics as chondrocytes and are differentiated into fibroblastic cells. Therefore, the present inventors have developed a culture apparatus and a culture method under a pressurized environment (Korean Patent Application No. 10-2018-0061111), which includes: a dish containing pressurized environmental cells disposed on a stage; and a transwell pressurizing the pressurized environmental cells cultured in the dish at a predetermined pressure, wherein the transwell includes a hollow chamber, a membrane composed of a porous film, and an alginate hydrogel attached to a lower portion of the membrane, thereby suppressing the dedifferentiation and promoting the redifferentiation of the pressurized environmental cells.

Furthermore, the present inventors have made intensive efforts to develop an effective anticancer agent using the incubator under the pressurized environment in order to overcome the limitations of traditional anticancer therapies and finally developed a method for the selective differentiation capable of differentiating to M1 macrophages, the method being effective in the development of cancer immunotherapeutic agent by pressurizing bone marrow-derived macrophages which are representative innate immune cells under appropriate pressure for a specific period of time (FIG. 1).

Hereinafter, the present invention will be described in more detail with reference to Examples. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Example 1: Testing Materials

The present inventors purchased undifferentiated macrophages (RAW 264.7, TIB-71, ATCC), and the undifferentiated macrophages were initially cultured at 37° C. using RPMI 1640 media (Gibco). The RAW 264.7 cells are undifferentiated macrophages having a characteristic in which the RAW 264.7 cells are attached to the surface of a cell culture dish and immediately differentiated into M0 macrophages.

The pressurizing device set forth in Korean Patent Application No. 10-2018-0061111 was used as a cell incubator under a pressurized environment to provide pressure for macrophages (FIG. 1). The incubator of pressurized environmental cells according to an embodiment of the inventive concept, as shown in FIG. 1, includes a dish 20 containing the pressurized environmental cells disposed on a stage 5; pressing unit 30; lifting platform 31; and a transwell 10 pressurizing the pressurized environmental cells cultured in the dish 20 at a predetermined pressure. Here, the transwell 10 may include a hollow chamber 11, support legs 15, a membrane which is provided in an upper side of an empty space of the chamber 11 and is composed of a porous film, and a hydrogel 13 attached to a lower portion of the membrane. The membrane may be a microporous film which is provided in the upper side of the empty space of the chamber 11, and a support in which a buffer solution, cellular substances, or culture media may be permeated but cells may not be permeated. The pore size of the membrane may be selected by a person skilled in the art, for example, 10 μm or less, and preferably, 0.4 μm to 8.0 μm. In addition, the membrane may be made of polycarbonate, polyester, and collagen-coated polytetrafluoroethylene. Meanwhile, the transwell 10 is substantially configured to pressurize the pressurized environmental cells, and the above-described predetermined pressure may be set differently according to parts of a body to be transplanted after completing incubating the pressurized environmental cells. In this case, the predetermined pressure set differently according to the pressurized environmental cells may be controlled by regulating the height (i.e., thickness) and concentration of the hydrogel 13. As the concentration of the hydrogel 13 is increased, the strength thereof may be increased, thereby forming a high pressure. Furthermore, the hydrogel 13 may have a weight for pressurizing the pressurized environmental cells at the above-described predetermined pressure in a state containing water or a culture liquid injected for incubating the pressurized environmental cells. That is, the weight of the hydrogel 13 is determined according to the above-described height (thickness) and concentration as well as the volume, at the same time considering the weight of water or the culture liquid contained in the hydrogel 13.

Figure 2:
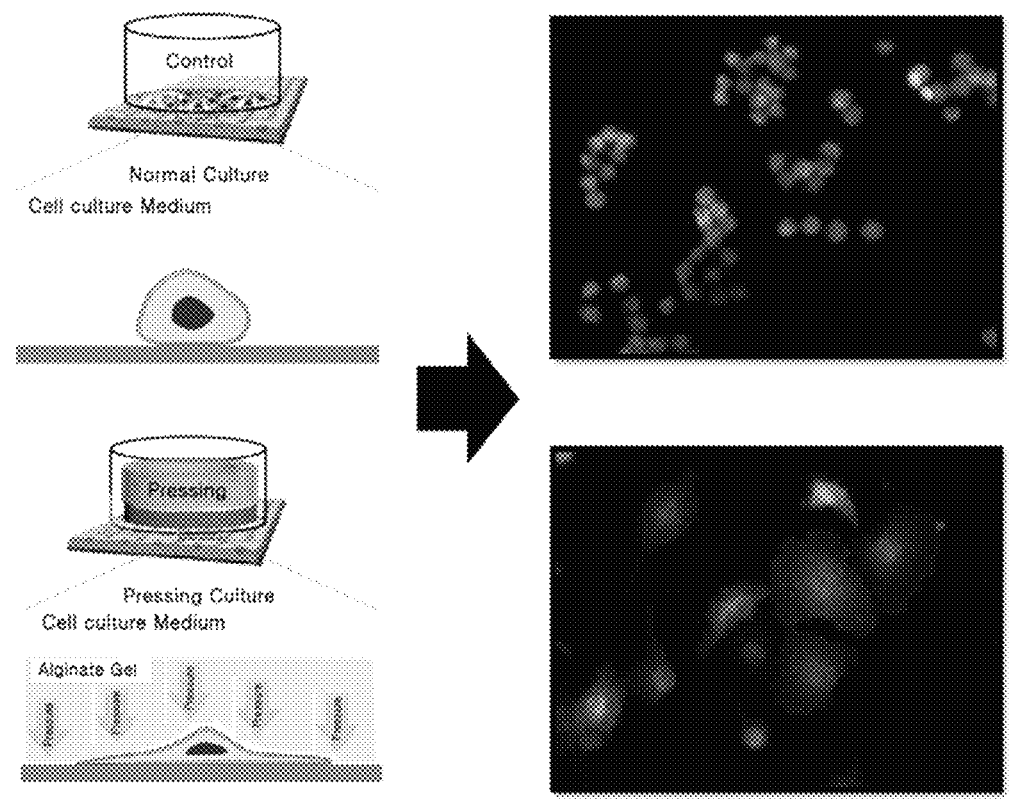
FIG. 2 is a schematic view illustrating a concept for a method for the selective differentiation to M1 macrophages in accordance with an exemplary embodiment of the present disclosure.
Figure 3:
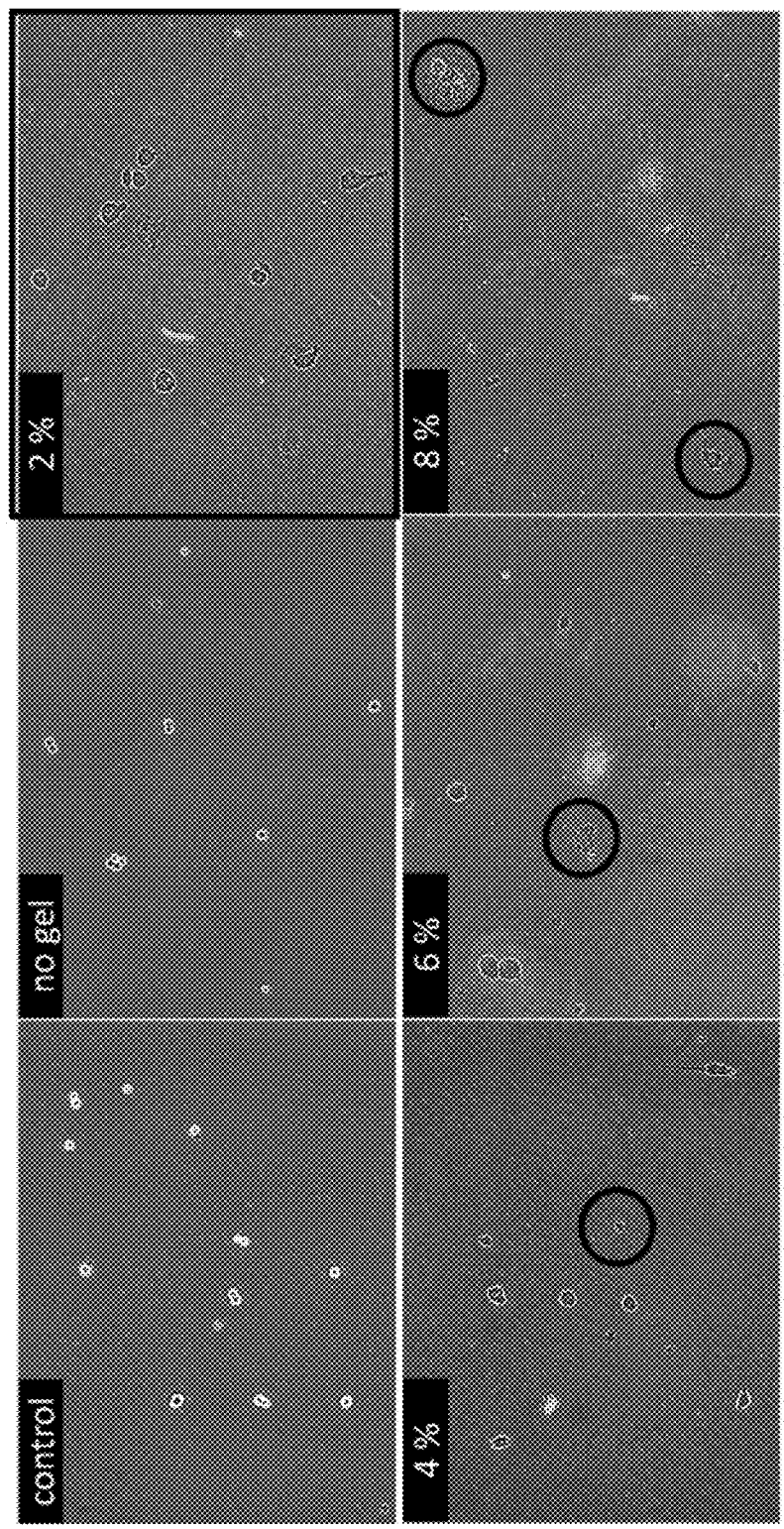
FIG. 3 is a photograph of observing cell death according to the concentration of alginate hydrogel of a pressurizing device.

As the hydrogel 13, any material to which cells are not attached and which has no cytotoxicity may be used. For example, the hydrogel 13 may be formed by hydration of a natural or synthetic polymer exhibiting a negative charge, and the natural or synthetic polymer may be carrageenan, alginate, xanthan gum, gellan gum, polyacrylic acid, heparin, or carboxymethylcellulose. The present inventors used an alginate hydrogel as an example of the hydrogel 13 (FIG. 2).

Example 2: Determination of Alginate Optimal Concentration

The present inventors determined the optimal concentration of the alginate hydrogel of the pressurizing device to provide pressure for the undifferentiated macrophages.

Specifically, 2%, 4%, 6%, and 8% sodium alginate (Sigma) each were added to sterile water and dissolved in an agitator for 24 hours, 500 μm of the mixture was uniformly distributed by pressing with the transwell, and then alginate hydrogel was gelated with calcium chloride solution (Sigma). Then, $1\times10^5$ of the incubated undifferentiated macrophages (RAW 264.7, TIB-71, ATCC) were attached to a 6-well plate, and incubated in RPMI 1640 media (Gibco) at 37° C. for 24 hours using the prepared alginate hydrogel.

As a result, cell death is observed in a gel concentration of greater than 2%, and thus the optimal concentration was determined to be 2%.

Example 3: Determination of Optimal Pressurizing Interval

To determine the optimal interval for providing pressure for macrophages, the present inventors incubated macrophages in the same conditions as in Example 2 except that pressure was applied to macrophages every 1, 3, 6, 12, and 24 hour intervals for 24 hours and 2% alginate hydrogel was used.

Figure 4:
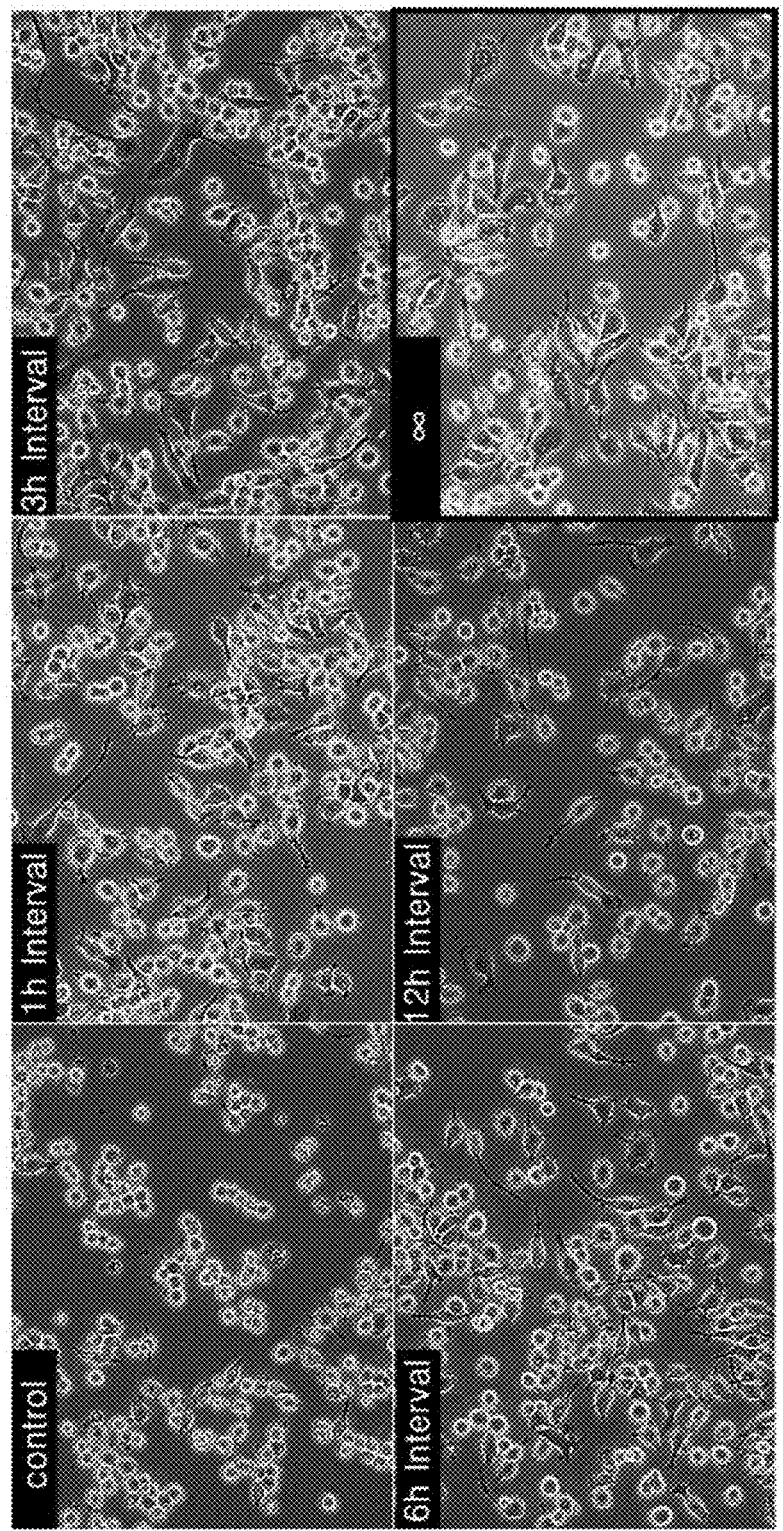
FIG. 4 is a photograph of observing cell proliferation according to time for which pressure is provided for macrophages.

As a result, it was confirmed that pressurizing macrophages for 24 hours was optimal (FIG. 4).

Example 4: Inhibition of Cell Proliferation

The present inventors observed whether or not inhibiting cell proliferation by pressurizing the undifferentiated macrophages. Specifically, while the macrophages were incubated in the same conditions as in Example 2 using 2% alginate hydrogel by pressurizing the macrophages for 24 hours, the macrophages were observed through a live cell optical microscope in real time.

Figure 5:
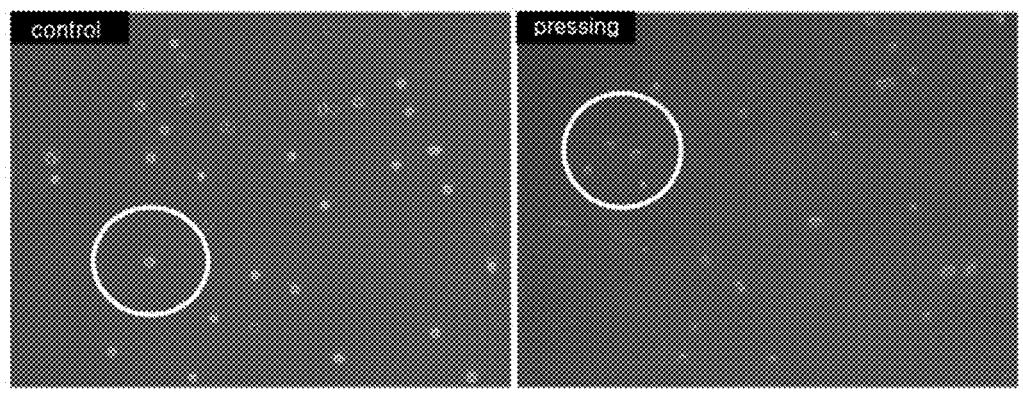
FIG. 5 is a photograph of observing whether or not inhibiting cell proliferation by providing pressure for macrophages.

As a result, the cell proliferation of the pressurized experimental group was inhibited compared to a control group. The above result suggests that pressurizing cells inhibits cell proliferation and promotes differentiation (FIG. 5).

Example 5: Phenotype and Size Variation

The present inventors observed the phenotype and size variation of macrophages by pressurizing the undifferentiated macrophages. Specifically, the undifferentiated macrophages were incubated in the same conditions as in Example 2 by using 2% alginate hydrogel and pressurizing the cells for 8 days and were observed through a phase-contrast microscope in 6 hours, 1, 3, 6, and 8 days interval.

Figure 6:
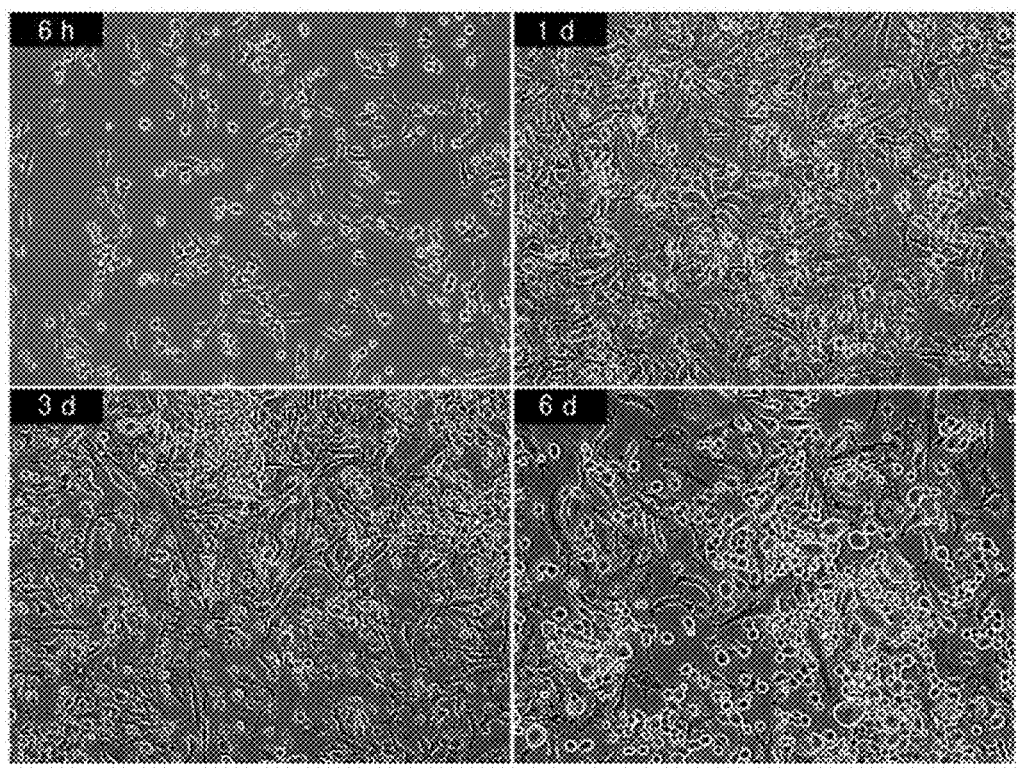
FIG. 6 is a photograph of observing phenotype and giant cells by providing pressure for macrophages.
Figure 7:
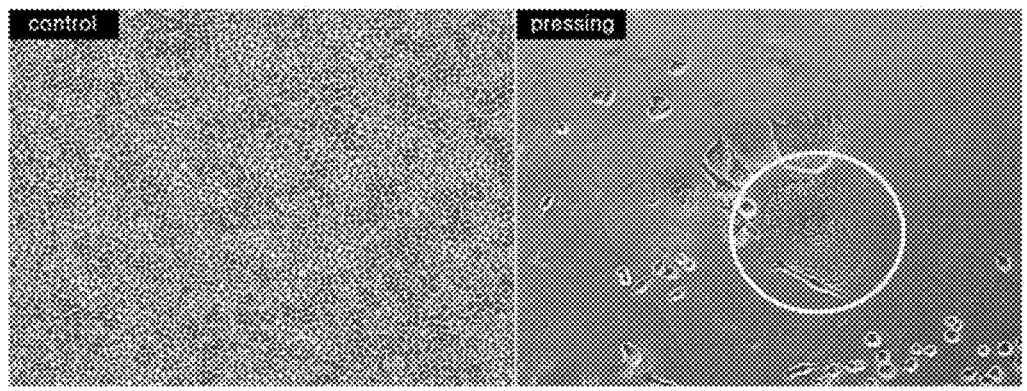
FIG. 7 is a photograph of observing phenotype and giant cells by providing pressure for macrophages.

As a result, after six days of pressurizing, giant cells having three or more nuclei were observed, and after eight days, giant cells having five nuclei were observed in a pressurized experimental group whereas only cell proliferation was observed in the control group (FIGS. 6 and 7).

Example 6: Observation in Hypoxia

The present inventors examined whether the pressurized environment causes hypoxia, thereby changing the phenotype and proliferation of the cells. To this end, the phenotype and size variation of the cells were observed by incubating the undifferentiated macrophages under hypoxia culture condition. Specifically, $1\times10^5$ of the incubated undifferentiated macrophages (RAW 264.7, TIB-71, ATCC) were attached to a 6-well plate, and then incubated in RPMI 1640 media (Gibco) at 37° C. at 1% oxygen concentration for 48 hours.

Figure 8:
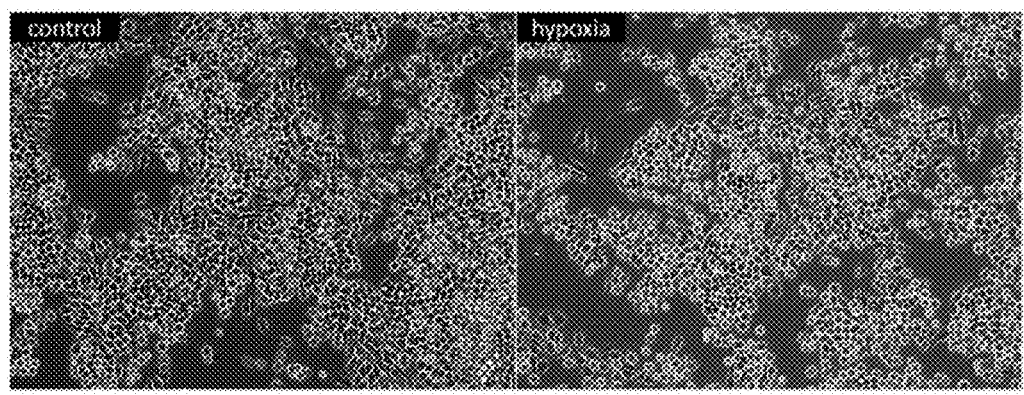
FIG. 8 is a photograph of observing phenotype and size variation of cells by pressurizing macrophages in hypoxia environment.

As a result, there was little change in the phenotype and proliferation of the control group and the experimental group in hypoxia (FIG. 8).

Example 7: Observation after Removing Gels

The present inventors observed the phenotype and size variation of the cells after pressurizing the undifferentiated macrophages for a certain period of time and removing gels. Specifically, the macrophages were incubated in the same conditions as in Example 2 after pressurizing the macrophages for five days using 2% alginate hydrogel, and the alginate hydrogel was removed.

Figure 9:
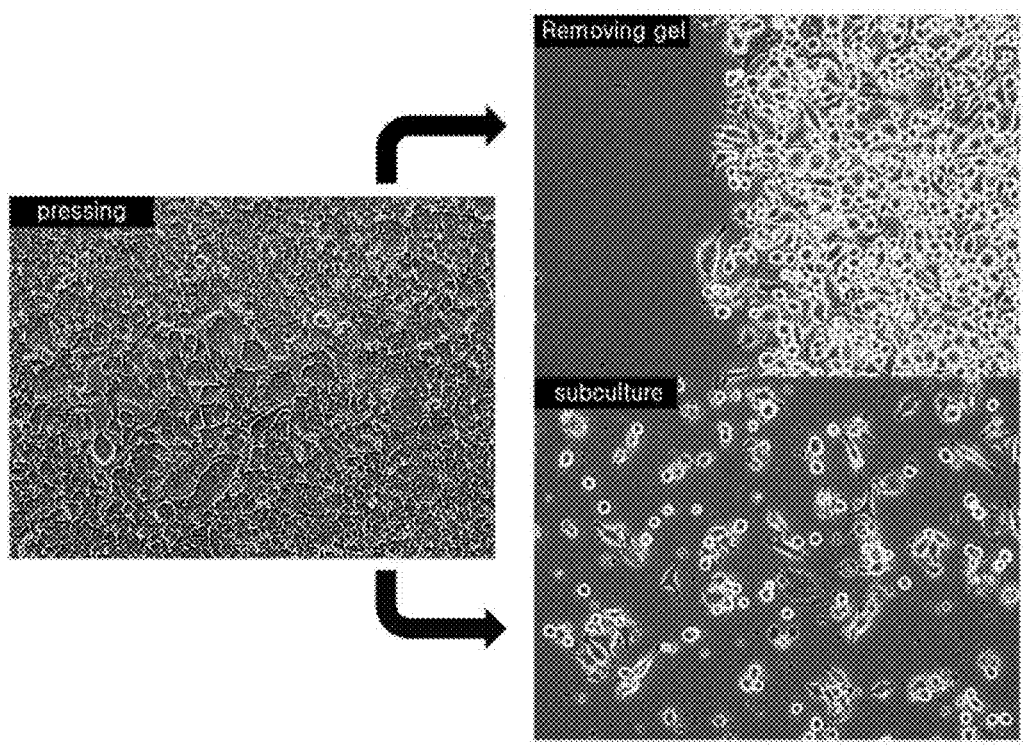
FIG. 9 is a photograph of observing phenotype and size variation of cells after providing pressure for macrophages and removing gels.
Figure 10:
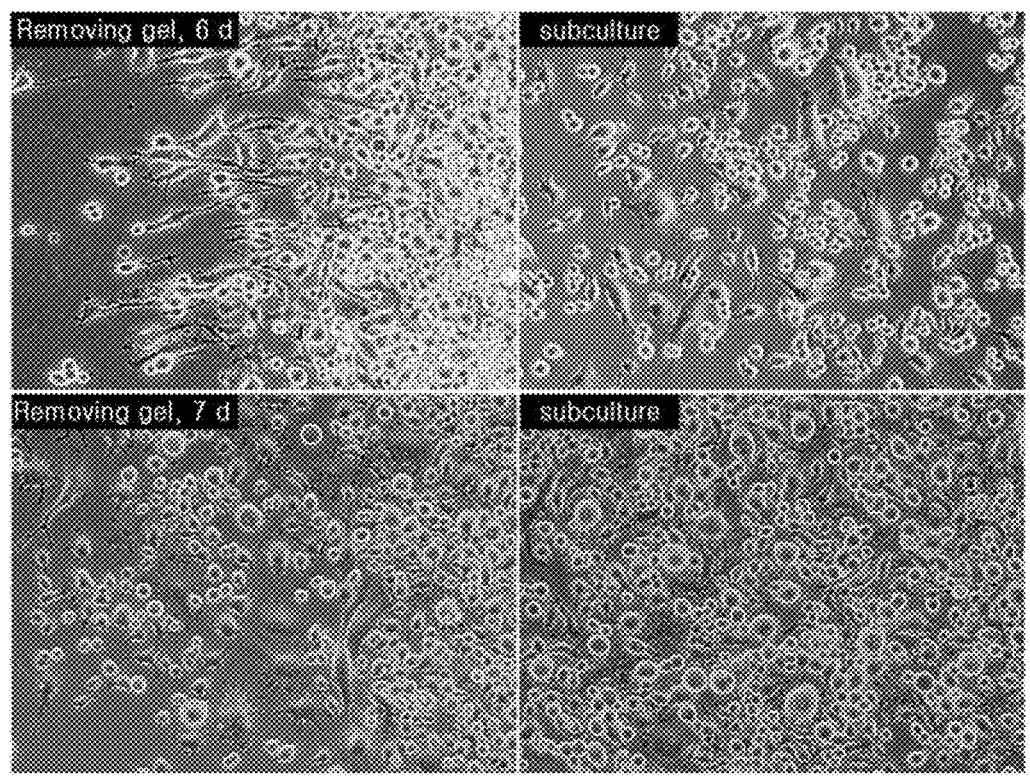
FIG. 10 is a photograph of observing phenotype and size variation of cells after providing pressure for macrophages and removing gels.

As a result, even though the gels were removed after pressurizing, the phenotype of the cells was maintained and the giant cells were observed (FIGS. 9 and 10). This suggests that when pressurizing conditions are maintained for a certain period of time, the differentiation of the cells occurs irreversibly.

Example 8: Observation of Thickness and Area of Cells

The present inventors observed the thickness and area of the cells through a scanning electron microscope and a phase-contrast microscope after pressurizing the macrophages. Specifically, the macrophages were pressurized for 6 hours by using 2% alginate hydrogel and incubated in the same conditions as in Example 2.

Figure 11:
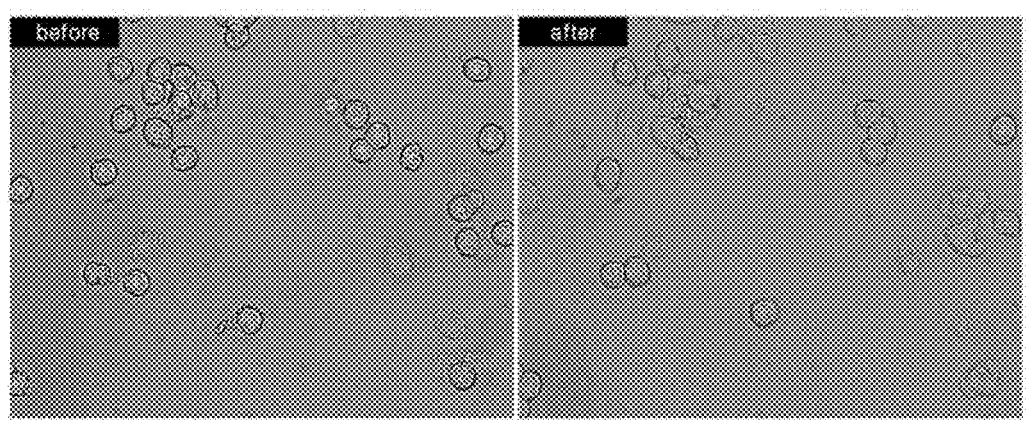
FIG. 11 is a photograph of observing area of cells after pressurizing macrophages.
Figure 12:
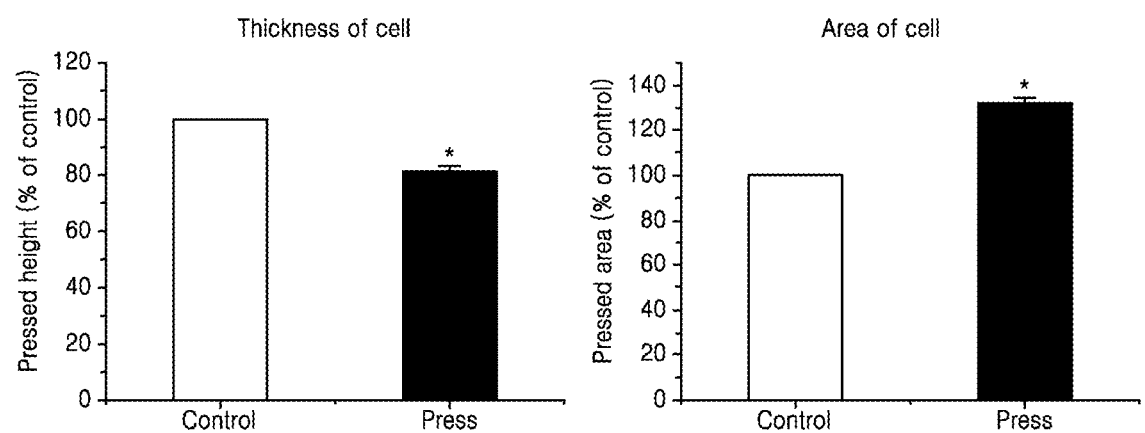
FIG. 12 is a graph analyzing thickness and area of cells after applying pressure to macrophages.

As a result, the thickness of the cells in the pressurized experimental group was decreased but area thereof was increased compared to the control group. This suggests that the alginate hydrogel provides a pressurized environment for the cells (FIGS. 11 and 12).

Example 9: Identification of Kinds of Differentiated Macrophages

The present inventors induced the differentiation of the undifferentiated macrophages by pressurizing the undifferentiated macrophages, and observed the size and phenotype of the cells. Specifically, the macrophages incubated in the same conditions as in Example 2 by pressurizing for 48 hours using 2% alginate hydrogel and the macrophages incubated in RPMI 1640 media (Gibco) at 37° C. for 48 hours using M1 cytokine (LPS, IFN-gamma, R&D systems) which can induce the macrophages into M1 were observed in comparison.

Figure 13:
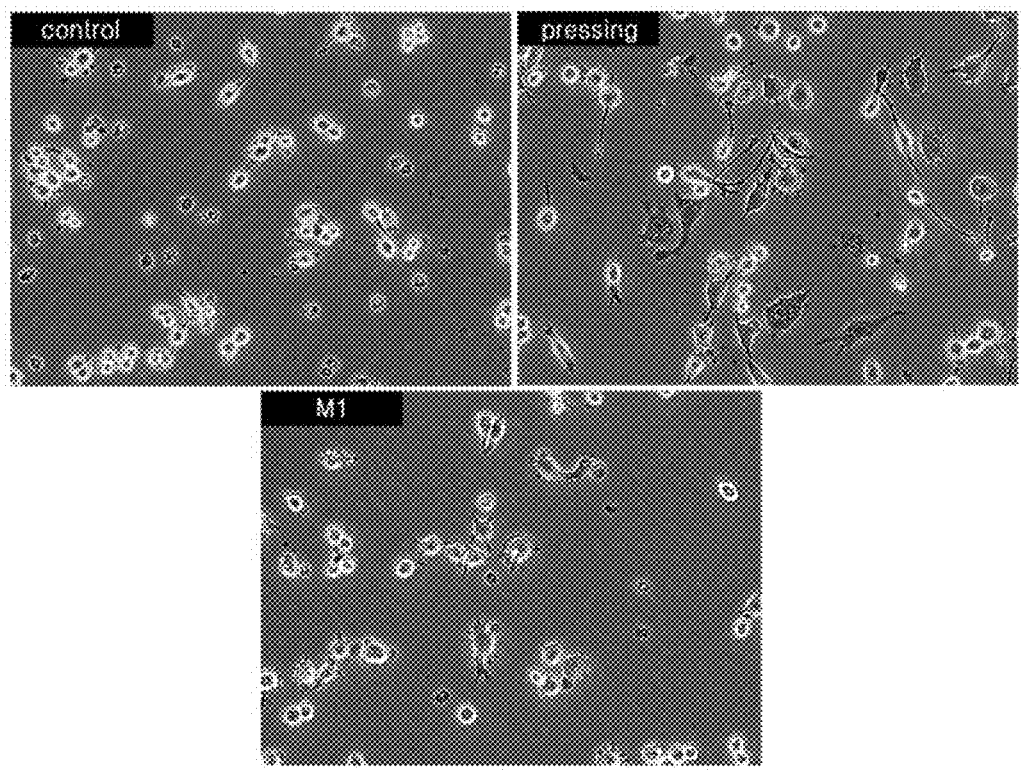
FIG. 13 is a photograph of observing phenotype and size of cells after pressurizing macrophages to induce differentiation into M1.

As a result, the macrophages in the pressurized experimental group were similar in the size and phenotype to the cells induced into M1 by cytokine (FIG. 13). This suggests that incubation of the undifferentiated macrophages in the pressurized environment of the inventive concept promotes M1-selective differentiation.

Example 10: Analysis of Marker Related to M1 Differentiation

The present inventors induced the differentiation of macrophages into M1 mitotic cells by pressurizing the macrophages, and then confirmed the expression profile of proteins through flow cytometry (FACS) and RT-PCR analysis to identify whether the differentiation-induced cells were actual M1 macrophages.

Specifically, the undifferentiated macrophages were incubated in the pressurized environment which were pressurized for two days or without being pressurized, and then FACS was performed by using an antibody specific for iNOS proteins as an M1 marker and an antibody specific for Arg1 proteins as an M2 marker, and RT-PCR was performed by using primer pairs which are HIF-1 as a hypoxia marker, NOS2 as an M1 marker, Arg1 as an M2 marker, and NFATc1 and TRAP mRNA as a osteoclast marker, which may be amplified respectively. The information of the primer pairs used in the RT-PCR is shown in Table 1 below.

TABLE 1

Information of Primer Pairs Used in RT-PCR

| Gene | Nucleic Acid Sequence (5'→3') | Tm | SEQ ID NO. |
| --- | --- | --- | --- |
| HIF-1 | Forward: CTT GAC AAG CTA GCC GGA GG | 59.5 | 1 |
|  | Reverse: TCG ACG TTC AGA ACT CAT CCT | 56.2 | 2 |
| NOS2 | Forward: TGC CAG GGT CAC AAC TTT ACA | 56.2 | 3 |
|  | Reverse: CTC TCC ACT GCC CCA GTT TT | 57.4 | 4 |
| Arg1 | Forward: ACG GCA GTG GCT TTA ACC TT | 55.4 | 5 |
|  | Reverse: AGG TAG TCA GTC CCT GGC TT | 57.4 | 6 |

TABLE 1-continued

Information of Primer Pairs Used in RT-PCR

| Gene | Nucleic Acid Sequence (5'→3') | Tm | SEQ ID NO. |
| --- | --- | --- | --- |
| NFATc1 | Forward: TTC GAG TTC GAT CAG AGC GG | 57.4 | 7 |
|  | Reverse: CGA GCC AGG TAT CTT CGG TC | 59.5 | 8 |
| TRAP | Forward: AGC AGC TCC CTA GAA GAT GGA | 58.2 | 9 |
|  | Reverse: GTA GGC AGT GAC CCC GTA TG | 59.5 | 10 |
| GAPDH | Forward: GGC AAA TTC AAC GGC ACA GT | 59.9 | 11 |
|  | Reverse: TAG GGC CTC TCT TGC TCA GT | 59.9 | 12 |

In addition, the cells were incubated in the same manner as in Example 10, and FACS and RT-PCR were performed by using the marker and primer pairs.

Figure 14:
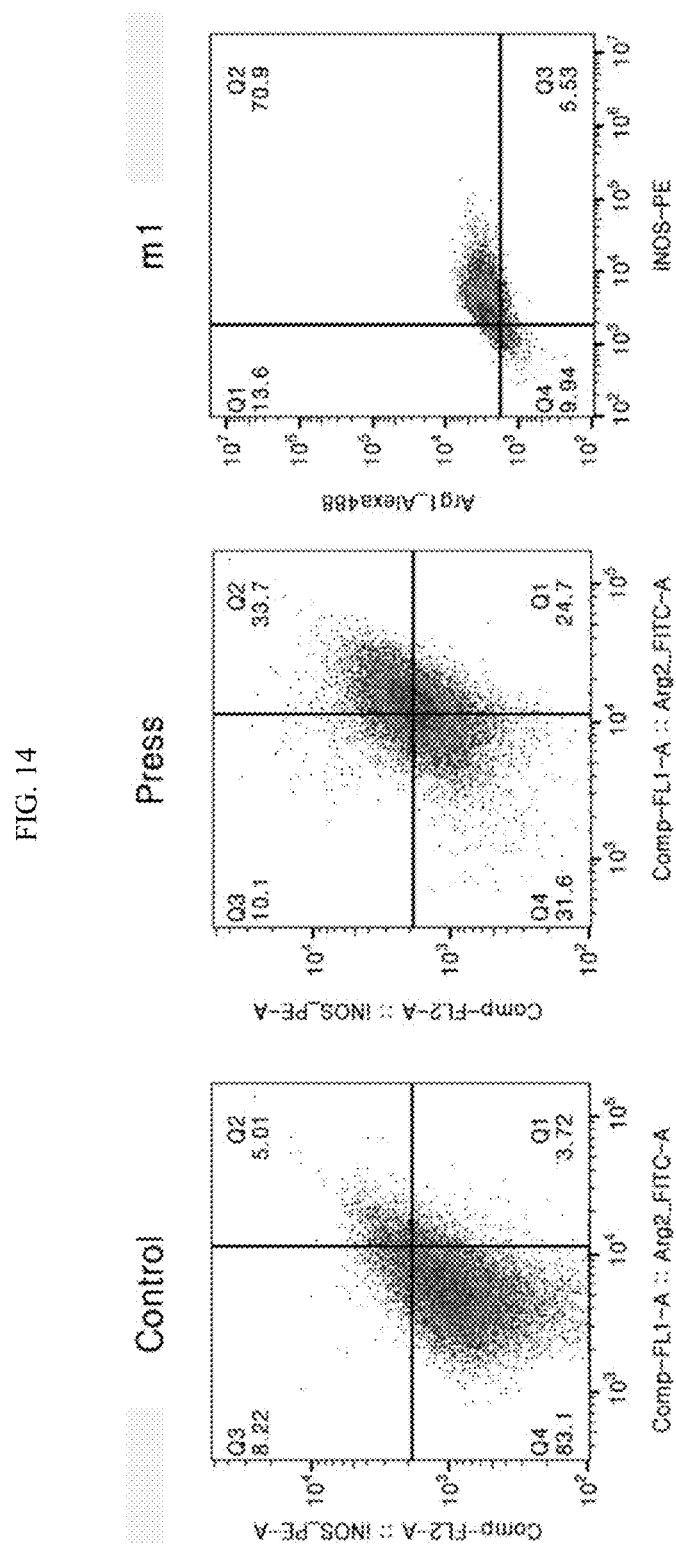
FIG. 14 is a two-dimensional histogram showing FACS results analyzing expression of related proteins after pressurizing macrophages to induce differentiation into M1.
Figure 15:
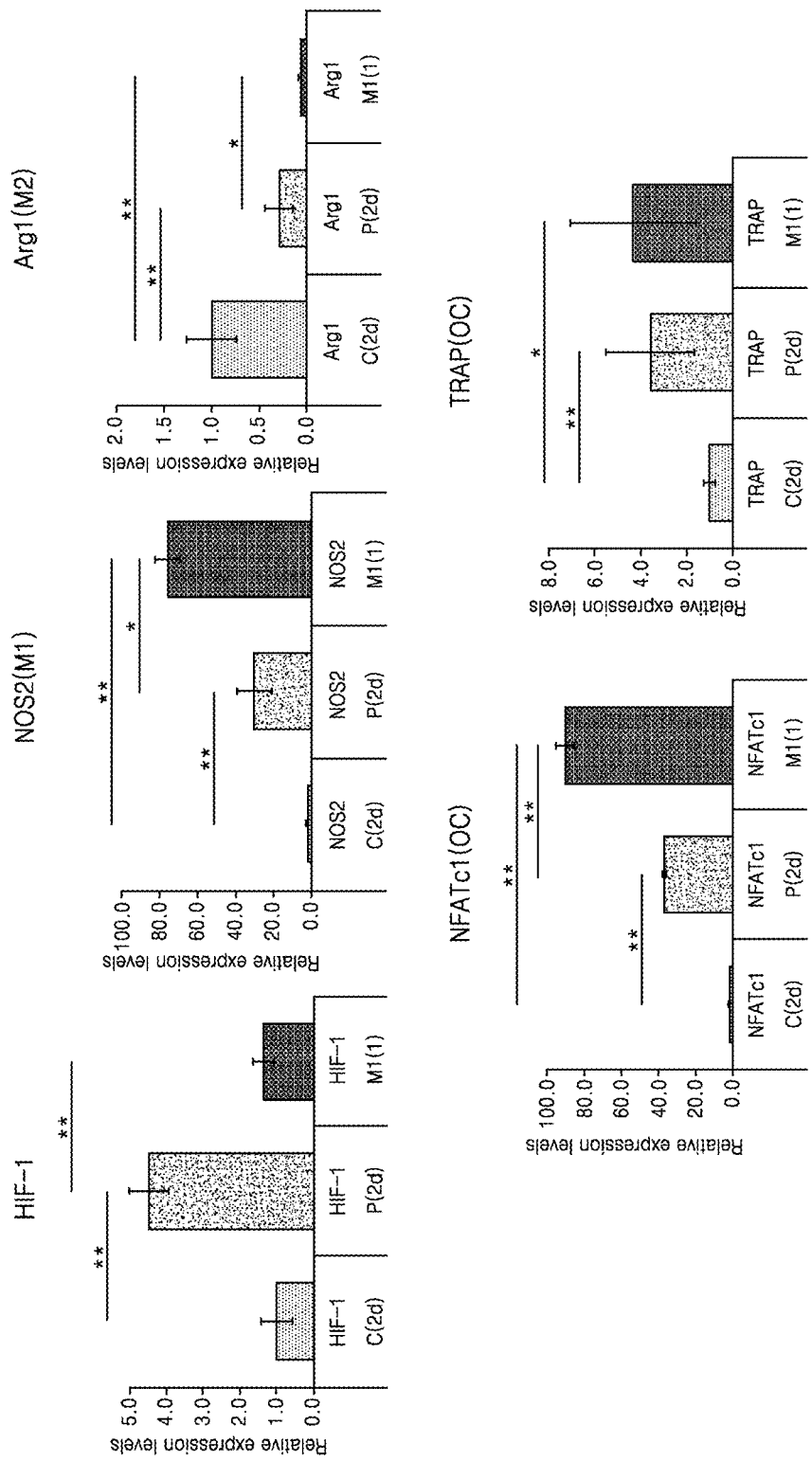
FIG. 15 is a PCR analysis graph of measuring expression of related proteins after pressurizing macrophages to induce differentiation into M1.

As a result, as shown in FIG. 15, it can be confirmed that the cells show the increase in the expression level of proteins similar to the cells induced into M1 (FIG. 14), and RT-PCR analysis shows little expression of genes related to M2, and the increase in expression of NOS2, a gene related to M1. It is interesting that the expression level of NFATc1 and TRAP which are genes related to osteoclast is increased, which is a sufficiently explainable phenomenon considering that the M1 macrophages have potential to ultimately differentiate into osteoclasts (FIG. 15).

Consequently, the method for the selective differentiation into M1 macrophages may selectively and effectively differentiate the undifferentiated macrophages into M1 macrophages which are innate immune cells playing important roles in anticancer and antimicrobial immune responses, and thus it is possible to utilize the method in the development of cancer immunotherapeutic agent having low side effects and excellent efficacy. In addition, since the M1 macrophages which are selectively differentiated according to an embodiment of the inventive concept are possibly differentiated into osteoclasts under appropriate conditions, it is possible to mass-produce osteoclasts which have been utilized only in the initial culture state due to absence of the established cell lines and to efficiently use the osteoclasts in the related studies such as therapeutic agents for osteoporosis.

As described above, an embodiment of the inventive concept may implement a method for the selective differentiation, the method being capable of efficiently differentiating into M1 macrophages which are innate immune cells important for anticancer and anti-inflammation responses by applying appropriate pressure to macrophages. In addition, the M1 macrophages may be used as an anticancer agent having low side effects and excellent efficacy. However, the scope of the present invention is not limited by such an effect.

The present invention is described with reference to the described examples, but the examples are merely illustrative. Therefore, it will be understood by those skilled in the art that various modifications and other equivalent embodiments can be made from the described embodiments. Hence, the real protective scope of the present invention shall be determined by the technical scope of the accompanying claims.

What is claimed is:

1. A method for selective differentiation of undifferentiated macrophages into M1 macrophages, the method comprising incubating the undifferentiated macrophages in an incubator under a pressurized environment;

wherein the pressurized environment is created by a transwell or a pressing plate which vertically descends from an upper portion of the incubator to the inside of the incubator to mechanically press the top surface of said undifferentiated macrophages at a pressure corresponding to atmospheric pressure of 1.5-5;

wherein the transwell comprises: a hollow chamber; and a membrane which is provided in an empty space of the chamber and is composed of a porous film;

wherein a hydrogel is attached to a bottom surface of the membrane or the pressing plate;

wherein the hydrogel is formed by hydration of alginate and a concentration of the alginate is 2%, and wherein the incubating the undifferentiated macrophages in the incubator under a pressurized environment is for at least 48 hours.

2. The method of claim 1, wherein the undifferentiated macrophages are monocyte-derived undifferentiated macrophages or bone marrow-derived undifferentiated macrophages.

\* \* \* \* \*